(12) United States Patent
Doussin et al.

(10) Patent No.: US 10,213,276 B2
(45) Date of Patent: Feb. 26, 2019

(54) INSERT FOR ULTRASONIC BURR-DRILL UNIT

(75) Inventors: Jean-Claude Doussin, Villenave d'Ornon (FR); Philippe Gangneux, Saint Loubes (FR); Jean-Michel Richer, Martignas (FR)

(73) Assignee: SOCIETE POUR LA CONCEPTIONS DES APPLICATIONS DES TECHNIQUES ELECTRONIQUES (SATELEC), Merignac (FR)

( * ) Notice: Subject to any disclaimer, the term of this patent is extended or adjusted under 35 U.S.C. 154(b) by 1504 days.

(21) Appl. No.: 11/597,994

(22) PCT Filed: Jun. 16, 2005

(86) PCT No.: PCT/FR2005/001508
§ 371 (c)(1),
(2), (4) Date: Mar. 2, 2007

(87) PCT Pub. No.: WO2005/102204
PCT Pub. Date: Nov. 3, 2005

(65) Prior Publication Data
US 2007/0254262 A1    Nov. 1, 2007

(30) Foreign Application Priority Data

Jun. 18, 2004 (FR) ...................................... 04 06630

(51) Int. Cl.
*A61C 3/03* (2006.01)
*A61B 90/92* (2016.01)

(52) U.S. Cl.
CPC ............... *A61C 3/03* (2013.01); *A61B 90/92* (2016.02); *A61C 2201/002* (2013.01)

(58) Field of Classification Search
CPC ........................... A61C 3/03; A61C 2201/002
USPC ...... 433/86, 119; 128/200.16; 451/165, 910; 318/116, 118; 604/22, 540, 542, 902; 606/170, 171, 172, 178; 81/DIG. 5
See application file for complete search history.

(56) References Cited

U.S. PATENT DOCUMENTS

| 3,990,452 A | 11/1976 | Murry et al. |
| 4,283,175 A * | 8/1981 | Nash ...................... A61C 17/20 433/119 |
| 4,811,736 A * | 3/1989 | Griggs ............... A61B 17/1633 606/170 |
| 4,911,639 A * | 3/1990 | Jacklich ................... A61C 1/07 433/102 |
| 4,984,985 A | 1/1991 | Edwardson |
| 5,941,706 A * | 8/1999 | Ura ........................ A61B 17/16 433/165 |

(Continued)

*Primary Examiner* — Matthew M Nelson
(74) *Attorney, Agent, or Firm* — Workman Nydegger

(57) ABSTRACT

In order to select the ultrasonic wave power and amplitude range that matches an ultrasonic tip (130) for mounting on a surgical handpiece (120), the tip (130) includes a cavity (131) forming a housing for an identifier element (140). The identifier element is made of an elastic material presenting a melting temperature higher than 130° C. enabling it to withstand both vibration and sterilization temperatures. The identifier element (140) presents a color or a pattern corresponding to the ultrasonic wave power and amplitude range appropriate for use with the tip.

13 Claims, 4 Drawing Sheets

(56) References Cited

U.S. PATENT DOCUMENTS

| | | | | |
|---|---|---|---|---|
| 6,039,567 | A * | 3/2000 | Abbott | A61C 3/025 |
| | | | | 433/88 |
| 6,047,618 | A * | 4/2000 | Pieri | 81/121.1 |
| 6,082,227 | A * | 7/2000 | Vogel | 81/119 |
| 6,193,515 | B1 * | 2/2001 | Rahman | A61C 3/00 |
| | | | | 433/141 |
| 6,312,256 | B1 | 11/2001 | Dieras et al. | |
| 6,328,566 | B1 * | 12/2001 | Feine | A61C 3/03 |
| | | | | 310/26 |
| 6,792,831 | B2 * | 9/2004 | Crosser | 81/119 |
| 6,912,937 | B2 * | 7/2005 | Tuanmu | 81/119 |
| 2003/0108844 | A1 * | 6/2003 | Rahman | A61C 1/07 |
| | | | | 433/119 |
| 2004/0098006 | A1 * | 5/2004 | Nakanishi | A61B 17/1631 |
| | | | | 606/170 |
| 2004/0191725 | A1 * | 9/2004 | Szymaitis | A61C 3/02 |
| | | | | 433/165 |

\* cited by examiner

INSERT FOR ULTRASONIC BURR-DRILL UNIT

BACKGROUND OF THE INVENTION

The present invention relates to appliances for dental treatment, and more particularly to ultrasonic appliances such as scaler appliances comprising instruments that vibrate at ultrasonic frequencies.

This type of appliance essentially comprises a handpiece including a transducer mechanically coupled to a vibrating instrument referred to as an "tip" or a "sonotrode", with the handpiece being connected to an ultrasound generator.

The tip is an interchangeable piece that presents a wide variety of shapes depending on the treatment for which it is intended. Examples of such tips are described in particular in U.S. Pat. Nos. 6,312,256 and 4,283,175. The amplitude or the power of the ultrasonic waves transmitted by the generator also depends on the type of treatment that is to be carried out. For example, for periodontal debridement, the required power/amplitude is well below that needed for removing scale ("scaling"). Similarly, the type of tip for periodontal debridement is different from that used for scaling. Consequently, for each type of dental treatment, there exist one or more families of tips that are designed to operate in with ultrasonic waves in a determined power and amplitude range.

At present, there exist dental treatment appliances that comprise an ultrasound generator of power that can be adjusted as a function of the treatment being carried out and as a function of the tip being used. In order to make such appliances easier for practitioners to use, the ultrasound generators are fitted with keys for automatically selecting a power range appropriate for the treatment. Those keys are identified by a color or equivalent code enabling the practitioner to select the appropriate power range.

Nevertheless, as mentioned above, tips are used that are specific to each kind of treatment and that are designed to operate in one of the preset power ranges on the appliance. Consequently, the practitioner must also verify that the tip placed on the handpiece does indeed match the selected power range, or conversely must select the power range that corresponds to the tip mounted on the handpiece. For this purpose, one of the prior art solutions consists in packaging each tip on a distinctive support element. The support element has markings that correspond to the marking on the keys for selecting power ranges. For example, if the keys are identified by a color code, then each support presents a color code corresponding to that of the key that serves to select the best power range for the tip placed on the support.

Nevertheless, that solution still presents drawbacks. Once the tip has been put into place on the handpiece, it is separated from its support, and consequently from the means that enable the appropriate power range to be identified. Thus, during treatment, it becomes difficult for the practitioner to make sure that the power range that has been selected does indeed match the tip present on the handpiece. In addition, since the support and the tip are separable, there exists a risk of a tip put onto a bad support, i.e. into a support that identifies a power range that does not match the tip, or vice versa.

Another solution consists in marking the tip by sticking on a label or by applying paint or varnish thereto. Nevertheless, that type of solution is unsatisfactory because of the severe conditions to which tips are subjected. In operation, the tip vibrates at frequencies of several tens of kilohertz and over amplitudes of several hundreds of micrometers, and it does so in moist environments. Furthermore, prior to each use, the tip must necessarily be sterilized in autoclave sterilizer appliances that generate temperatures around 130° C. Tip marking does not withstand such conditions of use and disappears very quickly.

OBJECT AND SUMMARY OF THE INVENTION

An object of the present invention is to propose a solution for identifying tips suitable for withstanding the conditions (vibration, temperature, . . . ) in which such instruments are used so as to provide means that are simple and reliable for verifying the power and amplitude range in which the tip can be used.

This object is achieved by an ultrasonic tip which, in accordance with the present invention, includes at least one cavity forming a housing for an identifier element, the identifier element being made of an elastic material that presents a melting temperature higher than 130° C.

Thus, the tip of the invention presents a design that enables it to be marked permanently, since the identifier means are integrated in the very structure of the tip. The cavity formed in the tip serves as a housing for the identifier element and prevents it from leaving the tip. The identifier element is made of an elastic material, thus enabling it to withstand the vibration of the tip. In addition, the material of the identifier element has a melting temperature higher than 130° so as to enable it to withstand sterilization temperatures.

One such material may be constituted in particular by polytetrafluoroethylene (PTFE) or by an elastomer.

In an embodiment of the invention, the cavity is an annular groove and the identifier element is a ring that is housed in the groove.

The cavity may also present a variety of shapes such as circular or oblong shapes, with the identifier element then presenting a shape that matches the shape of the cavity.

In an embodiment of the invention, the identifier element presents a color that corresponds to an ultrasonic wave power and amplitude range in which the tip is designed to operate. The color may be obtained in particular by incorporating a pigment as a filler in the material of the ring.

The cavity(ies) is/are preferably placed at a determined distance from the bottom end of the tip so as to project, at least in part, from the handpiece when the tip is mounted thereon. Thus, the identifier element housed in the cavity remains visible even when the tip is mounted on the handpiece.

The invention also provides an ultrasonic dental treatment appliance comprising at least one surgical handpiece connected to an ultrasound generator that includes means for selecting power and amplitude ranges for ultrasonic waves, the appliance further comprising at least one tip as described above.

The selector means of the ultrasound generator may be keys or the equivalent, each presenting a distinct color or pattern corresponding to a determined power and amplitude range.

BRIEF DESCRIPTION OF THE DRAWINGS

Other characteristics and advantages of the invention appear from the following description of particular embodiments of the invention given as non-limiting examples, and with reference to the accompanying drawings, in which.

DETAILED DESCRIPTION OF EMBODIMENTS OF THE INVENTION

Figure 1:
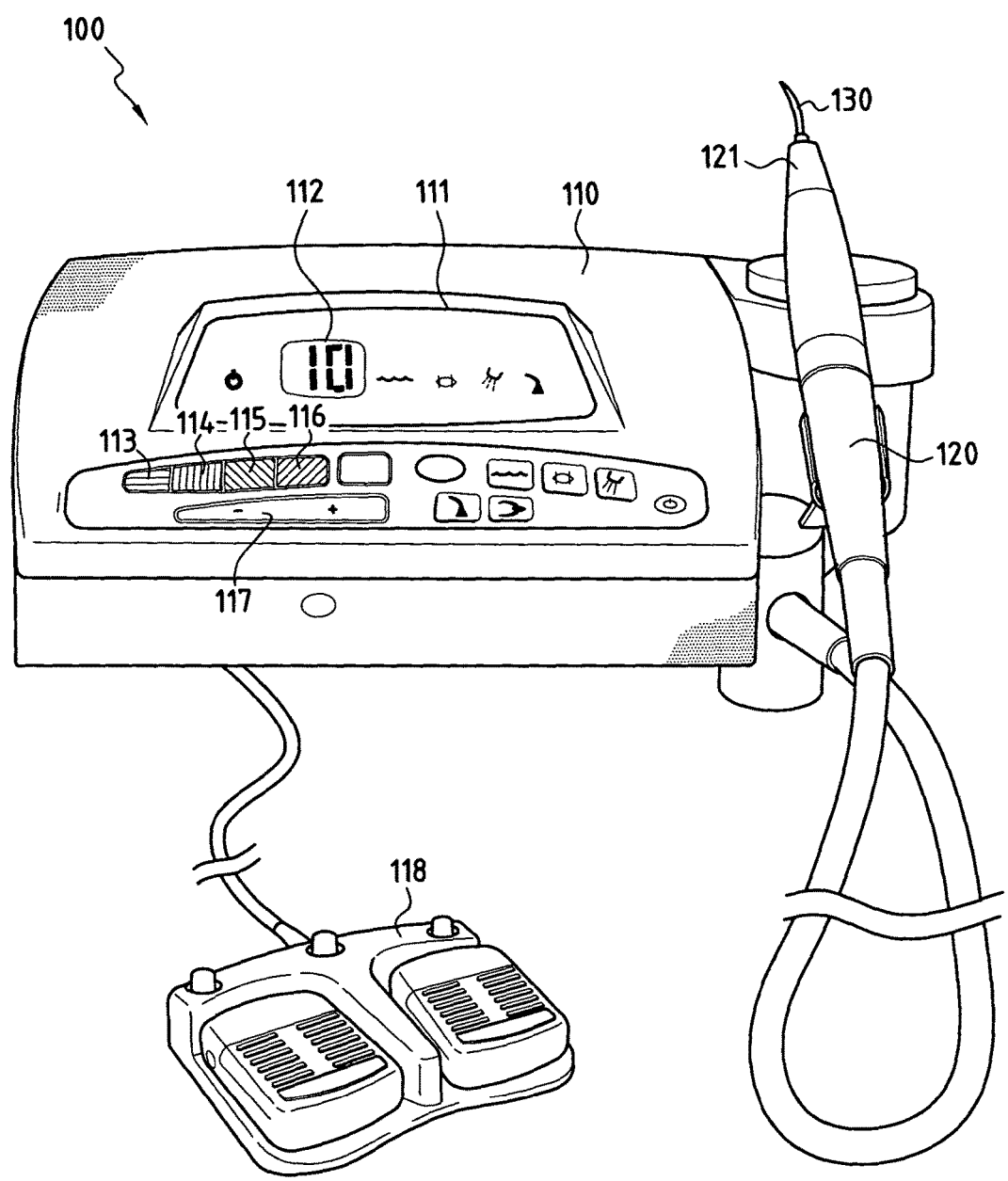
FIG. 1 is a perspective view of an ultrasonic scaler appliance constituting an embodiment of the invention.

FIG. 1 shows an ultrasound scaler appliance 100 comprising an ultrasound generator 110 connected to a handpiece 120 that is fitted with a tip 130. In well-known manner, the handpiece 120 includes a transducer (not shown), e.g. constituted by a piezoelectric material and mechanically coupled to the tip 130 in such a manner as to transmit vibratory waves thereto, the amplitude of the waves being determined as a function of the power delivered by the ultrasound generator 110.

The generator includes display means 111 and a series of keys 113 to 116, each corresponding to a determined power range. By way of example, the key 113, shaded in FIG. 1 with horizontal lines, corresponds to the lowest power and amplitude configuration, e.g. recommended for delicate treatment of fragile surfaces with very fine tips. The key 114, identified in FIG. 1 by vertical shading, corresponds to a medium power and amplitude range adapted for endodontonic applications using tips of thin and elongate shapes. Key 115, identified in FIG. 1 by right-sloping shading, corresponds to high power and amplitude levels adapted to prophylactic treatments such as scaling. The key 116, identified in the figure by left-sloping shading serves to select the maximum power and amplitude range, as can be necessary for example in apical surgery. In FIG. 1, the keys 113 to 116 are identified by each of the keys being patterned (shaded) differently. Nevertheless, any other recognition means could be used, for example a specific color for each key.

Thus, the generator 110 has means for selecting the best power range for various clinical applications. Once selected, the power range can be recognized by the corresponding key being lighted or by a special display on the generator, such as, for example, a screen 112 displaying the pattern or the color of the key on which the practitioner has pressed. In the selected power range, power can be adjusted by means of an adjustment key 117 or a pedal unit 118.

In order to identify tips as a function of the power and amplitude ranges that can be selected on the generator 110, the present invention proposes integrating marking in the very structure of the tip.

Figure 2:
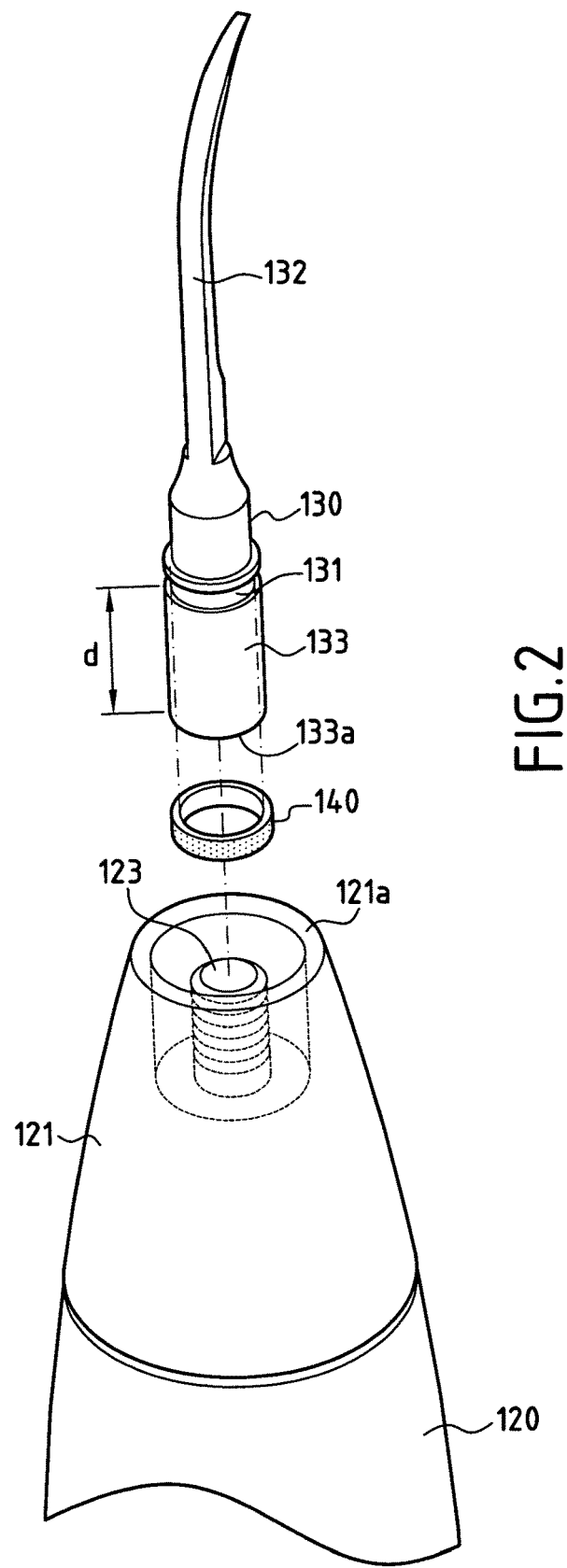
FIG. 2 is a perspective view, prior to mounting, of a tip constituting an embodiment of the invention.

FIG. 2 shows a tip 130 constituting a first embodiment of the present invention. The tip in this embodiment has an annular groove 131 that forms a housing for a ring 140 constituting the tip-identifier element.

The ring 140 is made of a material that is both capable of withstanding the ultrasonic vibration applied to tips and of withstanding the high temperatures of autoclave sterilizers, while also being biocompatible since the tip is for use when undertaking care or surgery in the mouths of patients. Any type of material satisfying these three properties can be suitable for making the identifier element, in this case the ring 140. One such material is polytetrafluoroethylene (PTFE), which is a material that is particularly well adapted to the use intended in the present invention. PTFE presents very high performance in terms of elongation at rupture (in the range 250% to 450%), elastic modulus (about 7500 kilograms per square centimeter ($kg/cm^2$)), and impact resistance (at least 16 kilogram-centimeters per centimeter ($kg \cdot cm/cm$)), thereby guaranteeing good resistance to the ultrasonic vibration of the tip. In addition, PTFE has thermal properties that are remarkable, since its melting temperature is 327° C., which is much higher than the temperatures encountered in autoclave sterilizers (around 130° C.). It also presents a coefficient of thermal expansion that is sufficiently small (about $10 \times 10^{-5}$ for temperatures in the range 23° C. to 60° C., and $21 \times 10^{-5}$ for temperatures lying in the range 100° C. to 200° C.) to prevent it from expanding under the effect of sterilization temperatures. Finally, PTFE is a leakproof material that is chemically and physiologically inert, and consequently it is biocompatible for medical applications. Other materials possessing similar properties could naturally be used for forming the ring 140. Amongst these materials, mention can be made of elastomers such as silicone.

In order to enable the tip to be identified visually, such as by recognizing a pattern or a color, the material constituting the ring 140 is subjected to additional treatment seeking to integrate therein the pattern or the color identical to that present on the key of the generator corresponding to the appropriate power range. For identification by means of color codes, the material of the ring is colored using dyes or pigments directly incorporated in the material. Thus, the color is present throughout the material and not only at its surface, thus making it possible to guarantee that the marking of the tip is permanent, even in the event of the exposed surface of the ring becoming worn or damaged. For example, with a ring made of PTFE, the PTFE is mixed with a pigment filler so as to give the ring the determined color.

Figure 3:
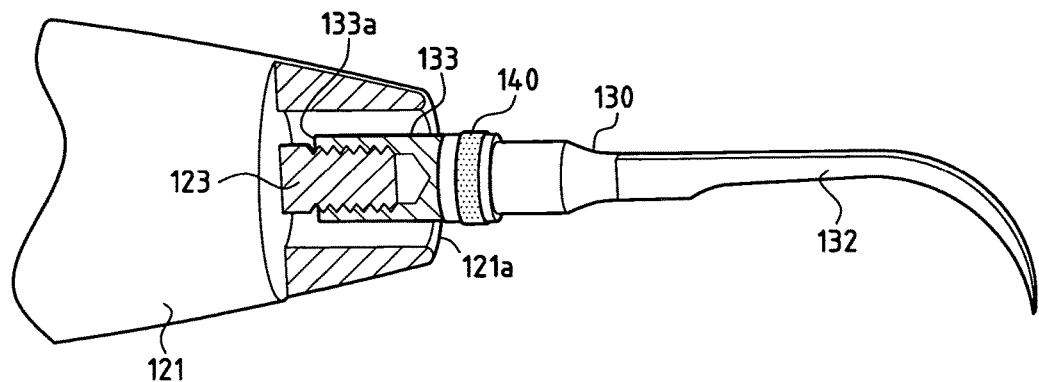
FIG. 3 is a view partially in section showing a tip constituting an embodiment of the invention, the tip being mounted on a handpiece.

As shown in FIGS. 2 and 3, the tip is screwed onto an element 123 secured to the transducer (not shown) of the handpiece 120. The element 123 is surrounded by a sleeve 121 that covers a portion of the base 133 of the tip when it is mounted on the handpiece. The groove 131 is preferably formed at a distance d from the bottom end 133a of the tip 130 that enables the ring to project beyond the edge 121a of the sleeve so as to remain visible even when the tip is mounted on the handpiece, as shown in FIG. 3.

Figure 4:
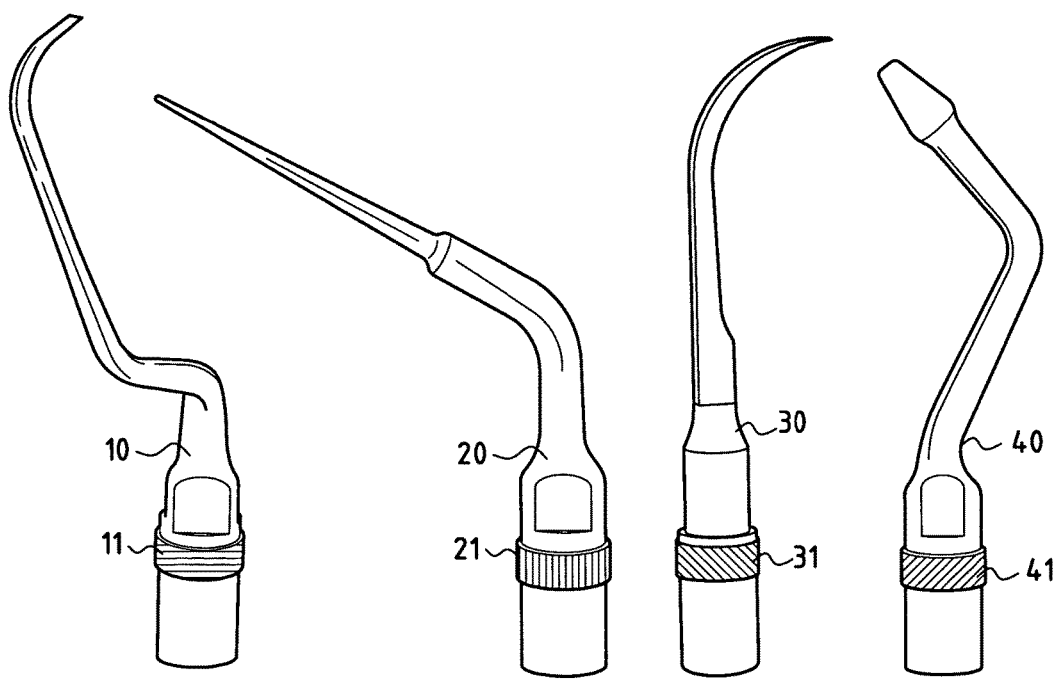
FIG. 4 is a perspective view of four variant embodiments of the tip of FIGS. 2 and 3.

Thus, in accordance with the invention, the power and amplitude range in which the tip is to be used can be clearly identified by the ring integrated in the structure of the tip. FIG. 4 shows four tips 10, 20, 30, and 40, each being designed to operate in a respective one of the four power and amplitude ranges available on the FIG. 1 ultrasound generator 100. As can be seen in FIG. 4, the tip 10 has a ring 11 presenting a pattern similar to that of the key 113 of the generator 100 of FIG. 1. The practitioner can thus easily identify the power and amplitude range in which the tip can be used. Similarly, each of the tips 20, 30, and 40 has its own operating range in terms of power and amplitude, and each has a respective ring 21, 31, or 41 presenting patterns that are identical to those of the keys 114, 115, or 116, respectively. Similarly, when identification is performed by using color codes, each of the rings 11, 12, 31, and 41 presents a different color that corresponds to the color of the associated key on the generator.

The solution implemented to mark tips in accordance with the invention is not limited to using an identifier element in the form of a ring housed in a circular groove as described above. The tip may have one or more cavities of a variety of shapes, housing respective identifier elements made of the same material as that used for the tip 140.

Figure 5:
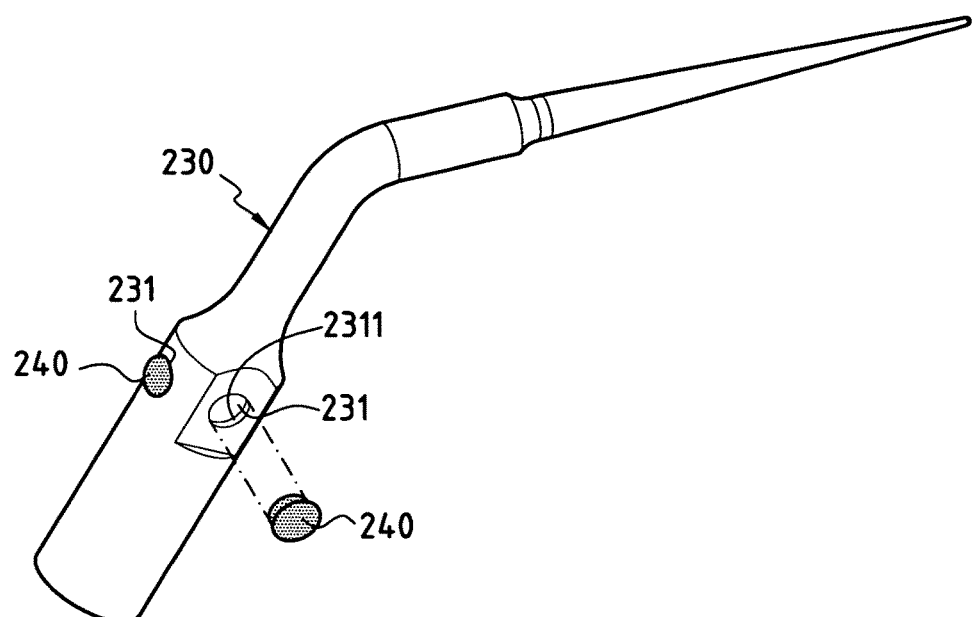
FIG. 5 is a perspective view of a tip in accordance with another embodiment of the invention.

FIG. 5 shows a tip 230 in another embodiment of the invention. Unlike the tips shown in FIGS. 3 and 4, the tip 230 does not have an annular ring, but instead has cavities 231 that are used for housing identifier elements in the form of pellets 240 that are formed like the ring 140 out of an elastic material having a melting temperature higher than 130° C. By way of particular example, the material may be PTFE that has been subjected to additional treatment (e.g. mixing the PTFE with a pigment filler) so as to incorporate therein the pattern or color identical to that present on the key of the generator, and corresponding to the appropriate power and amplitude range. The cavities 231 are formed in the tip 230 at a distance from the base of the tip that is sufficient to ensure they remain visible once the tip has been mounted on the handpiece.

Figure 6:
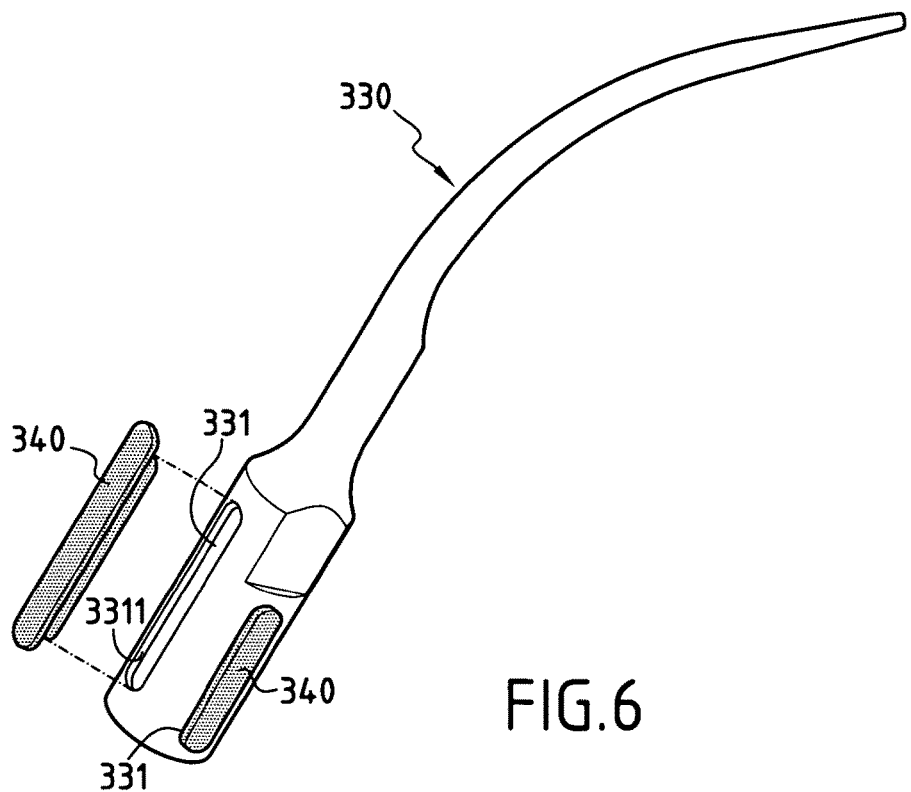
FIG. 6 is a perspective view of a tip in accordance with yet another embodiment of the invention.

In yet another embodiment of a tip having visual identification in accordance with the invention, the cavities and the identifier elements enabling the operating power and amplitude range of the tip to be identified visually can be oblong in shape. As shown in FIG. 6, a tip 330 has cavities 331 of oblong shape that serve as housings for identifier elements 340 that are likewise oblong in shape. The cavities 331 extend at a sufficient distance from the base of the tip to remain visible even when the tip is mounted on the handpiece.

In order to ensure that the pieces of elastic material are held securely, the cavities machined in the tip for providing housings for the identifier elements may present areas that are smaller than the areas of the bottoms of the cavities (e.g. cavities of tapering shape) so as to form a constriction towards the surface of the tip. In FIGS. 5 and 6, the edges 2311 and 3311 respectively of the cavities 231 and 331 may slope towards the bottoms of the cavities so that the area of a tip at the surface is smaller than its area at the bottom of a cavity. Under such circumstances, the piece of elastic material or the portion thereof for inserting into the cavity then presents dimensions that are close to those of the bottom of the cavity and the piece is inserted into a cavity by force. Thus, without a high level of traction being applied to the piece, the piece cannot escape from the cavity.

Retention of the identifier elements can be further improved by using adhesive between said elements and the cavities. With PTFE or silicone, for example, which are materials that are said to have "low surface energy", an appropriate adhesive should be used such as an acrylic adhesive.

The tips of the invention can be used with peripheral appliances for dental use such as the ultrasound treatment appliance of FIG. 1 which are functionally and ergonomically organized to constitute finished products. The tips can also be implemented with appliances that are in the form of modules for being integrated in other modules in dedicated products such as workstations for dental surgeries (i.e. OEM modules).

The invention claimed is:

1. An ultrasonic dental scaler appliance, comprising: at least one surgical handpiece connected to an ultrasound generator and at least one interchangeable ultrasound tip selectively mounted on the surgical handpiece, the tip consisting of:
   a first, treatment end having a distal end;
   a second, base end having a bottom end configured to be selectively mounted on the surgical handpiece; and
   at least one cavity forming a housing provided in the base end at a predetermined distance from the bottom end, such that the at least one cavity is located nearer the bottom end of the tip than the distal end, so as to project beyond the handpiece when the tip is mounted thereon so as to remain visible when the tip is mounted on the handpiece and during use thereof;
   wherein the tip is monolithically formed, and an identifier element is received within the housing, the identifier element made of an elastic material that has a melting temperature higher than 130° C.

2. An appliance according to claim 1, wherein the cavity is an annular groove and the identifier element is a ring housed in said annular groove.

3. An appliance according to claim 1, wherein the cavity is circular in shape and the identifier element is a pellet housed in said cavity.

4. An appliance according to claim 1, wherein the cavity is oblong in shape and identifier element is a piece having an oblong shape housed in said cavity.

5. An appliance according to claim 1, wherein the cavity has an area at the surface of the tip that is smaller than an area at the bottom of the cavity so as to form a constriction towards the surface of the tip.

6. An appliance according to claim 1, wherein the material of the identifier element is biocompatible.

7. An appliance according to claim 1, wherein the identifier element is made of polytetrafluoroethylene (PTFE).

8. An appliance according to claim 1, wherein the identifier element is made of elastomer.

9. An appliance according to claim 1, wherein the identifier element has a color corresponding to an ultrasonic wave power and amplitude range in which the tip is designed to operate.

10. An appliance according to claim 9, wherein the material of the identifier element includes a pigment filler so as to confer said corresponding color to the element.

11. An appliance according to claim 1, comprising means for selecting ultrasonic wave power and amplitude ranges.

12. An appliance according to claim 11, wherein the means for selecting the ultrasonic wave power and amplitude ranges comprises selection keys, each key presenting a distinct color or pattern corresponding to a determined power and amplitude range, and wherein the identifier element of the at least one ultrasound tip has a distinct color or pattern corresponding to an ultrasonic wave power and amplitude range in which the tip is designed to operate, and which corresponds to the distinct color or pattern of at least one selection key.

13. An appliance according to claim 1, wherein the base end, including the bottom end, has a uniform circumference outside of the at least one cavity.

* * * * *